United States Patent [19]
Draper et al.

[11] Patent Number: 5,514,577
[45] Date of Patent: May 7, 1996

[54] OLIGONUCLEOTIDE THERAPIES FOR MODULATING THE EFFECTS OF HERPESVIRUSES

[75] Inventors: Kenneth G. Draper, Boulder, Colo.; Stanley T. Crooke, Carlsbad, Calif.; Christopher K. Mirabelli, Encinitas, Calif.; David J. Ecker, Leucadia, Calif.; Ronnie C. Hanecak, San Clemente, Calif.; Kevin P. Anderson, Carlsbad, Calif.; Vickie L. Brown-Driver, San Diego, Calif.; Jacqueline R. Wyatt, Carlsbad, Calif.

[73] Assignee: Isis Pharmaceuticals, Inc., Carlsbad, Calif.

[21] Appl. No.: 31,147

[22] Filed: Mar. 12, 1993

Related U.S. Application Data

[63] Continuation-in-part of Ser. No. 485,297, Feb. 26, 1990, Pat. No. 5,248,670, and Ser. No. 852,132, Apr. 28, 1992, and Ser. No. 954,185, Sep. 29, 1992, abandoned.

[51] Int. Cl.$^6$ .............................. C12N 7/06; C07H 21/04
[52] U.S. Cl. ........................ 435/238; 536/23.1; 536/24.5; 514/44; 435/240.2; 935/34
[58] Field of Search .............................. 514/44; 536/23.1, 536/24.5; 435/6, 238

[56] References Cited

U.S. PATENT DOCUMENTS

| | | | |
|---|---|---|---|
| 4,689,320 | 8/1987 | Kaji ............................................. | 514/44 |
| 5,034,506 | 7/1991 | Summerton .............................. | 528/391 |

OTHER PUBLICATIONS

R N Ryan et al (1986) Microbiology 1986, Washington D.C., pp. 113–116.
R Weiss (1991) Science News 139: 108–109.
E Uhlmann et al (1990) Chemical Reviews 90(4): 569–571.
E R Kern (1990) Antiviral Agents and Viral Diseases of Man, Galasso et al, eds, pp. 94–95.
McGeoch, D. J., et al., "Complete DNA Sequence of the short repeat region in the genome of herpes simplex virus type 1," *Nucleic Acids Res.* 14:1727–1745, 1986.
McGeoch, D. J., et al., "The Complete DNA Sequence of the Long Unique Region in the Genome of Herpes Simplex Virus Type 1," *J. Gen. Virol.* 69:1531–1574, 1988.
Perry, L. J. and McGeoch, D. J., "The DNA Sequences of the Long Repeat Region and Adjoining Parts of the Long Unique Region in the Genome of Herpes Simplex Virus Type 1," *J. Gen. Virol.* 69:2831–2846, 1988.
Blair, E. D., et al., "Herpes Simplex Virus Virion Stimulatory Protein mRNA Leader Contains Sequence Elements Which Increase Both Virus–Induced Transcription and mRNA Stability," *J. Virol.* 61:2499–2508, 1987.
Ceruzzi, M, and Draper, K., "The Intracellular and Extracellular Fate of Oligodeoxyribonucleotides in Tissue Culture (List continued on next page.)

*Primary Examiner*—Jacqueline M. Stone
*Assistant Examiner*—Bruce R. Campell
*Attorney, Agent, or Firm*—Law Offices of Jane Massey Licata

[57] ABSTRACT

Compositions and methods are provided for the treatment and diagnosis of herpesvirus infections. In accordance with preferred embodiments, oligonucleotides are provided which are specifically hybridizable with RNA or DNA deriving from a herpesvirus gene corresponding to one of the open reading frames UL5, UL8, UL9, UL20, UL27, UL29, UL30, UL42, UL52 and IE175 of herpes simplex virus type 1. The oligonucleotide comprises nucleotide units sufficient in identity and number to effect said specific hybridization. In other preferred embodiments, the oligonucleotides are specifically hybridizable with a translation initiation site, a coding region or a 5'-untranslated region. Methods of treating animals suspected of being infected with herpesvirus comprising contacting the animal with an oligonucleotide of the invention are disclosed. Methods for treatment of infections caused by herpes simplex virus type 1, herpes simplex virus type 2, cytomegalovirus, human herpes virus 6, Epstein Barr virus or varicella zoster virus are disclosed.

2 Claims, 3 Drawing Sheets

OTHER PUBLICATIONS

Systems," *Nucleosides and Nucleotides* 8:815–818, 1989.

Mossmann, T., *J. Immunol. Methods.* 65:55, 1983.

Cai, W., et al. *J. Virol.* 62:2596–2604, 1988.

Kulka, M., et al., "Site specificity of the inhibitory effects of oligo (nucleoside methylphosphonate)s complementary to the acceptor splice junction of herpes simplex virus type 1 immediate early mRNA4," *Proc. Natl. Acad. Sci. USA* 86:6868–6872, 1989.

Smith, C. C., et al, "Antiviral effect of an oligo (nucleoside methylphosphonate) complementary to the splice junction of herpes simplex virus type 1 immediate early pre–mRNAs 4 and 5," *Proc. Natl. Acad. Sci. USA* 83:2787–2792, 1986.

Davison, A. J. & Scott, J. E., "The Complete DNA Sequence of Varicella–Zoster Virus," *J. Gen. Virol.* 67:1759–1816, 1987.

Baer, R., et al, "DNA sequence and expression of the B95–8 Epstein–Barr virus genome," *Nature* 310:207–211, 1984.

Davison, A. J. and McGeoch, D. J., *J. Gen Virol.* 67:597–611, 1986.

Davison, A. J. and Wilkie, N. M. *J. Gen. Virol.* 64:1927–1942, 1983.

P. E. Nielsen, et al. "Sequence–Selective Recognition of DNA by Strand Displacement with a Thymine–Substituted Polyamide," *Science* 254:1497, 1991.

McGeoch, D. J., et al., "Sequence Determination and Genetic Content of the Short Unique Region in the Genome of Herpes Simplex Virus Type 1," *J. Mol. Biol.* 181:1–13, 1985.

| HSV-1 | VCV | EBV |
|---|---|---|
| UL5 (6133-3485) | 55 (95996-98641) | BBLF4 (114259-111830) |
| UL8 (11478-9226) | 52 (90493-92808) | BBRF1 (114204-116045) |
| UL9 (14261-11706) | 51 (87881-90388) | BBRF2 (116045-119137) |
| UL13 (19504-17948) | 47 (83168-84700) | BGLF4 (123613-122325) |
| UL29 (53053-49463) | 29 (50857-54471) | BALF2 (164770-161384) |
| UL30 (53807-57514) | 28 (50636-47052) | BALF5 (156746-153701) |
| UL39 (77444-80857) | 19 (28845-26518) | BORF2 (76407-78887) |
| UL40 (80926-81948) | 18 (26493-25573) | BaRF1 (78900-79808) |
| UL42 (84113-85579) | 16 (23794-22568) | BMRF1 (79899-81113) |
| UL52 (100048-103224) | 6 (8577-5326) | BSLF1 (86879-84257) |

*Fig. 1*

SEQUENCE LISTING ( 1 ) GENERAL INFORMATION:

( i i i ) NUMBER OF SEQUENCES: 57

( 2 ) INFORMATION FOR SEQ ID NO: 1:

( i ) SEQUENCE CHARACTERISTICS:
    ( A ) LENGTH: 21
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 1:

CACGAAAGGC ATGACCGGGG C          21

( 2 ) INFORMATION FOR SEQ ID NO: 2:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 2:

CATGGCGGGA CTACGGGGC C          21

( 2 ) INFORMATION FOR SEQ ID NO: 3:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 3:

ACCGCCAGGG GAATCCGTCA T          21

( 2 ) INFORMATION FOR SEQ ID NO: 4:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 4:

GAGGTGGGCT TCGGTGGTGA          20

( 2 ) INFORMATION FOR SEQ ID NO: 5:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 5:

CATCGCCGAT GCGGGGCGAT C          21

( 2 ) INFORMATION FOR SEQ ID NO: 6:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear (i v) ANTI-SENSE: yes (x i) SEQUENCE DESCRIPTION: SEQ ID NO: 6:

GTTGGAGACC GGGGTTGGGG                    20

(2) INFORMATION FOR SEQ ID NO: 7:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 7:

CACGGGGTCG CCGATGAACC                    20

(2) INFORMATION FOR SEQ ID NO: 8:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 8:

GGGGTTGGGG AATGAATCCC                    20

(2) INFORMATION FOR SEQ ID NO: 9:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 9:

GGGTTGGAGA CCGGGGTTGG                    20

(2) INFORMATION FOR SEQ ID NO: 10:

(i) SEQUENCE CHARACTERISTICS:
        (A) LENGTH: 20
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 10:

GGTTGGAGAC CGGGGTTGGG                    20

(2) INFORMATION FOR SEQ ID NO: 11:

(i) SEQUENCE CHARACTERISTICS:
        (A) LENGTH: 20
        (B) TYPE: nucleid acid
        (C) STRANDEDNESS: single
        (D) TOPOLOGY: linear (i v) ANTI-SENSE: yes (x i) SEQUENCE DESCRIPTION: SEQ ID NO: 11:

TGGAGACCGG GGTTGGGGAA    20

( 2 ) INFORMATION FOR SEQ ID NO: 12:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: unknown ( i v ) ANTI-SENSE: yes ( x i ) SEQUENCE DESCRIPTION: SEQ ID NO: 12:

TTGGAGACCG GGGTTGGGGA    20

( 2 ) INFORMATION FOR SEQ ID NO: 13:

( i ) SEQUENCE CHARACTERISTICS:
        ( A ) LENGTH: 21
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 13:

GACGGTCAAG GGGAGGGTTG G    21

( 2 ) INFORMATION FOR SEQ ID NO: 14:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 14:

GGGGAGACCG AAACCGCAAA    20

( 2 ) INFORMATION FOR SEQ ID NO: 15:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 15:

CCTGGATGAT GCTGGGGTAC    20

( 2 ) INFORMATION FOR SEQ ID NO: 16:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( x i ) SEQUENCE DESCRIPTION: SEQ ID NO: 16:

GACTGGGGCG AGGTAGGGGT    20

( 2 ) INFORMATION FOR SEQ ID NO: 17:

( i ) SEQUENCE CHARACTERISTICS:
      ( A ) LENGTH: 20
      ( B ) TYPE: nucleic acid
      ( C ) STRANDEDNESS: single
      ( D ) TOPOLOGY: linear ( i v ) ANTI-SENSE: yes ( x i ) SEQUENCE DESCRIPTION: SEQ ID NO: 17:

GTCCCGACTG GGGCGAGGAT          20

( 2 ) INFORMATION FOR SEQ ID NO: 18:

( i ) SEQUENCE CHARACTERISTICS:
      ( A ) LENGTH: 18
      ( B ) TYPE: nucleic acid
      ( C ) STRANDEDNESS: single
      ( D ) TOPOLOGY: linear ( i v ) ANTI-SENSE: yes ( x i ) SEQUENCE DESCRIPTION: SEQ ID NO: 18:

GAAAGGCATG ACCGGGGC          18

( 2 ) INFORMATION FOR SEQ ID NO: 19:

( i ) SEQUENCE CHARACTERISTICS:
      ( A ) LENGTH: 15
      ( B ) TYPE: nucleic acid
      ( C ) STRANDEDNESS: single
      ( D ) TOPOLOGY: linear ( i v ) ANTI-SENSE: yes ( x i ) SEQUENCE DESCRIPTION: SEQ ID NO: 19:

AGGCATGACC GGGGC          15

( 2 ) INFORMATION FOR SEQ ID NO: 20:

( i ) SEQUENCE CHARACTERISTICS:
      ( A ) LENGTH: 12
      ( B ) TYPE: nucleic acid
      ( C ) STRANDEDNESS: single
      ( D ) TOPOLOGY: linear ( i v ) ANTI-SENSE: yes ( x i ) SEQUENCE DESCRIPTION: SEQ ID NO: 20:

CATGACCGGG GC          12

( 2 ) INFORMATION FOR SEQ ID NO: 21:

( i ) SEQUENCE CHARACTERISTICS:
      ( A ) LENGTH: 21
      ( B ) TYPE: nucleic acid
      ( C ) STRANDEDNESS: single
      ( D ) TOPOLOGY: linear ( i v ) ANTI-SENSE: yes ( x i ) SEQUENCE DESCRIPTION: SEQ ID NO: 21:

GCCGAGGTCC ATGTCGTACG C          21

( 2 ) INFORMATION FOR SEQ ID NO: 22:

( i ) SEQUENCE CHARACTERISTICS:
      ( A ) LENGTH: 18
      ( B ) TYPE: nucleic acid
      ( C ) STRANDEDNESS: single
      ( D ) TOPOLOGY: linear (i v) ANTI-SENSE: yes (x i) SEQUENCE DESCRIPTION: SEQ ID NO: 22:

CACGAAAGGC ATGACCGG                    18

(2) INFORMATION FOR SEQ ID NO: 23:

(i) SEQUENCE CHARACTERISTICS:
        (A) LENGTH: 15
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 23:

CACGAAAGGC ATGAC                       15

(2) INFORMATION FOR SEQ ID NO: 24:

(i) SEQUENCE CHARACTERISTICS:
        (A) LENGTH: 18
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 24:

TGGCGGGACT ACGGGGGC                    18

(2) INFORMATION FOR SEQ ID NO: 25:

(i) SEQUENCE CHARACTERISTICS:
        (A) LENGTH: 15
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 25:

CATGGCGGGA CTACG                       15

(2) INFORMATION FOR SEQ ID NO: 26:

(i) SEQUENCE CHARACTERISTICS:
        (A) LENGTH: 15
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 26:

GGCGGGACTA CGGGG                       15

(2) INFORMATION FOR SEQ ID NO: 27:

(i) SEQUENCE CHARACTERISTICS:
        (A) LENGTH: 18
        (B) TYPE: nucleic acid
        (C) STRANDEDNESS: single
        (D) TOPOLOGY: linear (i v) ANTI-SENSE: yes (x i) SEQUENCE DESCRIPTION: SEQ ID NO: 27:

GCCAGGGGAA TCCGTCAT                18

(2) INFORMATION FOR SEQ ID NO: 28:

(i) SEQUENCE CHARACTERISTICS:
        (A) LENGTH: 15
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 28:

AGGGGAATCC GTCAT                   15

(2) INFORMATION FOR SEQ ID NO: 29:

(i) SEQUENCE CHARACTERISTICS:
        (A) LENGTH: 15
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 29:

GCCAGGGGAA TCCGT                   15

(2) INFORMATION FOR SEQ ID NO: 30:

(i) SEQUENCE CHARACTERISTICS:
        (A) LENGTH: 18
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 30:

CATCGCCGAT GCGGGGCG                18

(2) INFORMATION FOR SEQ ID NO: 31:

(i) SEQUENCE CHARACTERISTICS:
        (A) LENGTH: 15
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 31:

CATCGCCGAT GCGGG                   15

(2) INFORMATION FOR SEQ ID NO: 32:

(i) SEQUENCE CHARACTERISTICS:
        (A) LENGTH: 15
        (B) TYPE: nucleic acid
        (C) STRANDEDNESS: single
        (D) TOPOLOGY: linear (iv) ANTI-SENSE: yes (xi) SEQUENCE DESCRIPTION: SEQ ID NO: 32:

CGCCGATGCG GGGCG                   15

(2) INFORMATION FOR SEQ ID NO: 33:

(i) SEQUENCE CHARACTERISTICS:
    (A) LENGTH: 12
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 33:

GCCGATGCGG GG                   12

(2) INFORMATION FOR SEQ ID NO: 34:

(i) SEQUENCE CHARACTERISTICS:
    (A) LENGTH: 17
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 34:

GGAGACCGGG GTTGGGG              17

(2) INFORMATION FOR SEQ ID NO: 35:

(i) SEQUENCE CHARACTERISTICS:
    (A) LENGTH: 17
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 35:

GTTGGAGACC GGGGTTG              17

(2) INFORMATION FOR SEQ ID NO: 36:

(i) SEQUENCE CHARACTERISTICS:
    (A) LENGTH: 15
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 36:

AGACCGGGGT TGGGG                15

(2) INFORMATION FOR SEQ ID NO: 37:

(i) SEQUENCE CHARACTERISTICS:
    (A) LENGTH: 10
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 37:

GGGGTTGGGG                      10

(2) INFORMATION FOR SEQ ID NO: 38:

(i) SEQUENCE CHARACTERISTICS:
    (A) LENGTH: 16
    (B) TYPE: nucleic acid
    (C) STRANDEDNESS: single
    (D) TOPOLOGY: linear (iv) ANTI-SENSE: yes (xi) SEQUENCE DESCRIPTION: SEQ ID NO: 38:

GAGACCGGGG TTGGGG        16

(2) INFORMATION FOR SEQ ID NO: 39:

(i) SEQUENCE CHARACTERISTICS:
      (A) LENGTH: 17
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 39:

GGGGTCGCCG ATGAACC        17

(2) INFORMATION FOR SEQ ID NO: 40:

(i) SEQUENCE CHARACTERISTICS:
      (A) LENGTH: 15
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 40:

CACGGGGTCG CCGAT        15

(2) INFORMATION FOR SEQ ID NO: 41:

(i) SEQUENCE CHARACTERISTICS:
      (A) LENGTH: 17
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 41:

CACGGGGTCG CCGATGA        17

(2) INFORMATION FOR SEQ ID NO: 42:

(i) SEQUENCE CHARACTERISTICS:
      (A) LENGTH: 10
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 42:

CACGGGGTCG        10

(2) INFORMATION FOR SEQ ID NO: 43:

(i) SEQUENCE CHARACTERISTICS:
      (A) LENGTH: 21
      (B) TYPE: nucleic acid
      (C) STRANDEDNESS: single
      (D) TOPOLOGY: linear (iv) ANTI-SENSE: yes (xi) SEQUENCE DESCRIPTION: SEQ ID NO: 43:

GCCGAGGTCC ATGTCGTACG C                     21

(2) INFORMATION FOR SEQ ID NO: 44:

(i) SEQUENCE CHARACTERISTICS:
      (A) LENGTH: 21
      (B) TYPE: nucleic acid
      (C) STRANDEDNESS: single
      (D) TOPOLOGY: linear (iv) ANTI-SENSE: no (xi) SEQUENCE DESCRIPTION: SEQ ID NO: 44:

TGGGCACGTG CCTGACACGG C                     21

(2) INFORMATION FOR SEQ ID NO: 45:

(i) SEQUENCE CHARACTERISTICS:
      (A) LENGTH: 21
      (B) TYPE: nucleic acid
      (C) STRANDEDNESS: single
      (D) TOPOLOGY: linear (iv) ANTI-SENSE: yes (ix) FEATURE:
      (A) NAME/KEY: Modified-site
      (B) LOCATION: 18
      (D) OTHER INFORMATION: modified base is inosine.

(xi) SEQUENCE DESCRIPTION: SEQ ID NO: 45:

CACGAAAGGC ATGACCGNGG C                     21

(2) INFORMATION FOR SEQ ID NO: 46:

(i) SEQUENCE CHARACTERISTICS:
      (A) LENGTH: 21
      (B) TYPE: nucleic acid
      (C) STRANDEDNESS: single
      (D) TOPOLOGY: linear (iv) ANTI-SENSE: yes (ix) FEATURE:
      (A) NAME/KEY: Modified-site
      (B) LOCATION: 20
      (D) OTHER INFORMATION: modified base is inosine.

(xi) SEQUENCE DESCRIPTION: SEQ ID NO: 46:

CACGAAAGGC ATGACCGGGN C                     21

(2) INFORMATION FOR SEQ ID NO: 47:

(i) SEQUENCE CHARACTERISTICS:
      (A) LENGTH: 20
      (B) TYPE: nucleic acid
      (C) STRANDEDNESS: single
      (D) TOPOLOGY: linear (iv) ANTI-SENSE: yes (ix) FEATURE:
      (A) NAME/KEY: Modified-site
      (B) LOCATION: 13
      (D) OTHER INFORMATION: modified base is inosine.

(ix) FEATURE:
      (A) NAME/KEY: Modified-site
      (B) LOCATION: 19
      (D) OTHER INFORMATION: modified base is inosine.

(xi) SEQUENCE DESCRIPTION: SEQ ID NO: 47:

GTTGGAGACC GGNGTTGGNG                    20

( 2 ) INFORMATION FOR SEQ ID NO: 48:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( i x ) FEATURE:
        ( A ) NAME/KEY: Modified-site
        ( B ) LOCATION: 14
        ( D ) OTHER INFORMATION: modified base is inosine.

( x i ) SEQUENCE DESCRIPTION: SEQ ID NO: 48:

GTTGGAGACC GGGNTTGGGG                    20

( 2 ) INFORMATION FOR SEQ ID NO: 49:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( i x ) FEATURE:
        ( A ) NAME/KEY: Modified-site
        ( B ) LOCATION: 19
        ( D ) OTHER INFORMATION: modified base is inosine.

( x i ) SEQUENCE DESCRIPTION: SEQ ID NO: 49:

GTTGGAGACC GGGGTTGGNG                    20

( 2 ) INFORMATION FOR SEQ ID NO: 50:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( i x ) FEATURE:
        ( A ) NAME/KEY: Modified-site
        ( B ) LOCATION: 12
        ( D ) OTHER INFORMATION: modified base is inosine.

( x i ) SEQUENCE DESCRIPTION: SEQ ID NO: 50:

GTTGGAGACC GNGGTTGGGG                    20

( 2 ) INFORMATION FOR SEQ ID NO: 51:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i v ) ANTI-SENSE: yes ( i x ) FEATURE:
        ( A ) NAME/KEY: Modified-site
        ( B ) LOCATION: 20
        ( D ) OTHER INFORMATION: modified base is inosine.

( x i ) SEQUENCE DESCRIPTION: SEQ ID NO: 51:

GTTGGAGACC GGGGTTGGGN                    20

( 2 ) INFORMATION FOR SEQ ID NO: 52:

( i ) SEQUENCE CHARACTERISTICS:
           ( A ) LENGTH: 24
           ( B ) TYPE: nucleic acid
           ( C ) STRANDEDNESS: single
           ( D ) TOPOLOGY: linear ( i v ) ANTI-SENSE: yes ( x i ) SEQUENCE DESCRIPTION: SEQ ID NO: 52:

TTGGGGTTGG GGTTGGGGTT GGGG               24

( 2 ) INFORMATION FOR SEQ ID NO: 53:

( i ) SEQUENCE CHARACTERISTICS:
           ( A ) LENGTH: 12
           ( B ) TYPE: nucleic acid
           ( C ) STRANDEDNESS: single
           ( D ) TOPOLOGY: linear ( i v ) ANTI-SENSE: yes ( x i ) SEQUENCE DESCRIPTION: SEQ ID NO: 53:

TTGGGGTTGG GG                            12

( 2 ) INFORMATION FOR SEQ ID NO: 54:

( i ) SEQUENCE CHARACTERISTICS:
           ( A ) LENGTH: 8
           ( B ) TYPE: nucleic acid
           ( C ) STRANDEDNESS: single
           ( D ) TOPOLOGY: linear ( i v ) ANTI-SENSE: yes ( x i ) SEQUENCE DESCRIPTION: SEQ ID NO: 54:

TTGGGGTT                                 8

( 2 ) INFORMATION FOR SEQ ID NO: 55:

( i ) SEQUENCE CHARACTERISTICS:
           ( A ) LENGTH: 20
           ( B ) TYPE: nucleic acid
           ( C ) STRANDEDNESS: single
           ( D ) TOPOLOGY: linear ( i v ) ANTI-SENSE: yes ( x i ) SEQUENCE DESCRIPTION: SEQ ID NO: 55:

TTGGGGTTGG GGTTGGGGTT                    20

( 2 ) INFORMATION FOR SEQ ID NO: 56:

( i ) SEQUENCE CHARACTERISTICS:
           ( A ) LENGTH: 16
           ( B ) TYPE: nucleic acid
           ( C ) STRANDEDNESS: single
           ( D ) TOPOLOGY: linear ( i v ) ANTI-SENSE: yes ( x i ) SEQUENCE DESCRIPTION: SEQ ID NO: 56:

GGGGTTGGGG TTGGGG                        16

( 2 ) INFORMATION FOR SEQ ID NO: 57:

-continued ( i ) SEQUENCE CHARACTERISTICS:
    ( A ) LENGTH: 18
    ( B ) TYPE: nucleic acid
    ( C ) STRANDEDNESS: single
    ( D ) TOPOLOGY: linear ( i v ) ANTI-SENSE: yes ( x i ) SEQUENCE DESCRIPTION: SEQ ID NO: 57:

TTGGGGTTGG GGTTGGGG        18

OLIGONUCLEOTIDE THERAPIES FOR MODULATING THE EFFECTS OF HERPESVIRUSES

FIELD OF THE INVENTION

This invention relates to therapies and diagnostics for herpesvirus infections. In particular, this invention relates to oligonucleotide interactions with certain portions of herpesvirus RNA which have been found to lead to modulation of the activity of the RNA and, thus, to modulation of the effects of the viruses themselves. This application is a continuation-in-part of U.S. Ser. No. 485,297, U.S. Pat. No. 5,248,670, filed Feb. 26, 1990; U.S. Ser. No. 852,132, filed Apr. 28, 1992; and U.S. Ser. No. 954,185, abandoned, filed Sep. 29, 1992, each of which applications is assigned to the assignee of the present invention.

BACKGROUND OF THE INVENTION

Approximately 500,000 new cases of genital herpes are reported each year, and it is estimated that 30 million Americans are affected by this currently incurable disease. Similarly, it is estimated that there is an annual incidence of 500,000 new cases of herpes simplex gingivostomatitis and at least 100 million Americans suffer from recurrent herpes labialis. Overall the prevalence of seropositive individuals in the general population is approximately 70–80%. Although recurrent herpes simplex virus infections are the most prevalent of all herpesvirus infections, there is a need to develop more specific forms of therapy for diseases such as herpes simplex encephalitis, keratoconjunctivitis, herpetic whitlow and disseminated herpes infections of neonates and immunocompromised hosts.

The incidence of encephalitis is low (one case in 250,000 individuals per year), yet with existing therapy, the mortality rate is as high as 40% and approximately 50% of the survivors are left with severe neurological sequelae. Ocular infections are neither rare nor trivial. They are usually caused by herpes simplex virus (HSV) type 1 (HSV-1) and are a leading cause of blindness in many countries of the world. Herpetic whitlow is an occupational hazard of nurses, dentists and physicians which begins with erythema and tenderness of the distal segments of the fingers and is followed by coalescence and enlargement of the vesicles. An accompanying lymphangitis and lymphadenopathy of the draining lymphatics is a common feature. Neonatal HSV infection is usually encountered as a consequence of a child being born through an infected birth canal. The incidence of the disease is approximately 1 in 10,000 births. Mortality in babies with limited infection can be as high as 20% while mortality of neonates from disseminated infection, even with current therapy, can approach 75% and many survivors have significant neurological impairment.

Currently, nucleoside analogs are clearly the preferred therapeutic agents for HSV infections. A number of pyrimidine deoxyribonucleoside compounds have a specific affinity for the virus-encoded thymidine (dCyd) kinase enzyme. The specificity of action of these compounds confines the phosphorylation and antiviral activity of these compounds to virus-infected cells. A number of drugs from this class, e.g., 5-iodo-dUrd (IDU), 5-trifluoro-methyl-dUrd (FMAU), 5-ethyl-dUrd (EDU), (E)-5-(2-bromovinyl)-dUrd (BVDU), 5-iodo-dCyd (IDC), and 5-trifluoromethyl-dUrd (TFT), are either in clinical use or likely to become available for clinical use in the near future. IDU is a moderately effective topical antiviral agent when applied to HSV gingivostomatitis and ocular stromal keratitis, however, its use in controlled clinical studies of HSV encephalitis revealed a high toxicity associated with IDU treatment. Although the antiviral specificity of 5-arabinofuranosyl cytosine (Ara-C) was initially promising, its clinical history has paralleled that of IDU. The clinical appearance of HSV strains which are deficient in their ability to synthesize the viral thymidine kinase has generated further concern over the future efficacy of this class of compounds.

The utility of a number of viral targets has been defined for anti-HSV compound development. Studies with thiosemicarbazone compounds have demonstrated that inhibition of the viral ribonucleotide reductase enzyme is an effective means of inhibiting replication of HSV in vitro. Further, a number of purine nucleosides which interfere with viral DNA replication have been approved for treatment of human HSV infections. 9-($\beta$-D-arabinofuranosyl) adenine (Ara-A) has been used for treatment of HSV-1 keratitis, HSV-1 encephalitis and neonatal herpes infections. Reports of clinical efficacy are contradictory and a major disadvantage for practical use is the extremely poor solubility of Ara-A in water. 9-(2-hydroxyethoxymethyl) guanine (Acyclovir, ACV) is of major interest. In humans, ACV has been used successfully in the therapy of localized and disseminated HSV infections. However, there appear to be both the existence of drug-resistant viral mutants and negative results in double-blind studies of HSV-1 treatment with ACV. ACV, like Ara-A, is poorly soluble in water (0.2%) and this physical characteristic limits the application forms for ACV. The practical application of purine nucleoside analogs in an extended clinical situation suffers from their inherently efficient catabolism, which not only lowers the biological activity of the drug but also may result in the formation of toxic catabolites.

All of the effective anti-HSV compounds currently in use or clinical testing are nucleoside analogs. The efficacy of these compounds is diminished by their inherently poor solubility in aqueous solutions, rapid intracellular catabolism and high cellular toxicities. An additional caveat to the long-term use of any given nucleoside analog is the recent detection of clinical isolates of HSV which are resistant to inhibition by nucleoside compounds which were being administered in clinical trials. Antiviral oligonucleotides offer the potential of better compound solubilities, lower cellular toxicities and less sensitivity to nucleotide point mutations in the target gene than those typical of the nucleoside analogs.

It is apparent that new routes to the diagnosis and therapy of herpesvirus infections are greatly desired. It is particularly desired to provide compositions and methods for therapy which are, at once, highly effective and free of serious side effects. Thus, the provision of oligonucleotide therapies for herpesvirus infections in accordance with this invention satisfies the long-felt need for such therapies.

OBJECTS OF THE INVENTION

It is a principal object of the invention to provide therapies for herpesvirus and other virus infections.

It is a further object of the invention to provide oligonucleotides which are capable of modulating the function of RNA of herpesviruses and other viruses.

Yet another object is to secure means for diagnosis of herpesvirus and related virus infection.

These and other objects of this invention will become apparent from a review of the instant specification.

3

SUMMARY OF THE INVENTION

In accordance with the present invention, oligonucleotides are provided which are specifically hybridizable with RNA or DNA deriving from a gene corresponding to one of the open reading frames UL5, UL8, UL9, UL20, UL27, UL29, UL30, UL42, UL52 and IE175 of herpes simplex virus type 1. The oligonucleotide comprises nucleotide units sufficient in identity and number to effect such specific hybridization. It is preferred that the oligonucleotides be specifically hybridizable with a translation initiation site, coding region or 5' untranslated region.

In accordance with preferred embodiments, the oligonucleotides are designed to be specifically hybridizable with DNA or even more preferably, RNA from one of the species herpes simplex virus type 1 (HSV-1), herpes simplex virus type (HSV-2), cytomegalovirus, human herpes virus 6, Epstein Barr virus (EBV) or varicella zoster virus (VZV). Such oligonucleotides are conveniently and desirably presented as a pharmaceutical composition in a pharmaceutically acceptable carrier.

In accordance with other preferred embodiments, the oligonucleotides comprise one or more modifications which confer desired characteristics, such as, for example, improved uptake into cells, stability to nucleases, improved binding to RNA, and the like.

Other aspects of the invention are directed to methods for diagnostics and therapeutics of animals, especially humans, suspected of having a herpesvirus or other virus infection. Such methods comprise contacting the animal or cells, tissues or a bodily fluid of the animal with oligonucleotides in accordance with the invention in order to inhibit the proliferation or effect of such infection, or to effect a diagnosis thereof.

Persons of ordinary skill in the art will recognize that the particular open reading frames described for herpes simplex virus type 1 find counterparts in the other viruses named. Thus each of herpes simplex virus type 2, cytomegalovirus, human herpes virus type 6, Epstein Barr virus and varicella zoster virus are believed to have many analogous open reading frames which code for proteins having similar functions. Accordingly, the present invention is directed to antisense oligonucleotide therapy in which the oligonucleotides are directed to any of the foregoing viruses, or indeed to any similar viruses which may become known hereafter, which have one or more of such analogous open reading frames. For convenience in connection with the present invention, all such viruses are denominated as herpesviruses.

BRIEF DESCRIPTION OF THE DRAWINGS

FIG. 1 is a tabulation of the homologous ORFS among HSV-1, VZV, and EBV as predicted from published DNA sequence data.

DETAILED DESCRIPTION OF THE INVENTION

Figure 2:
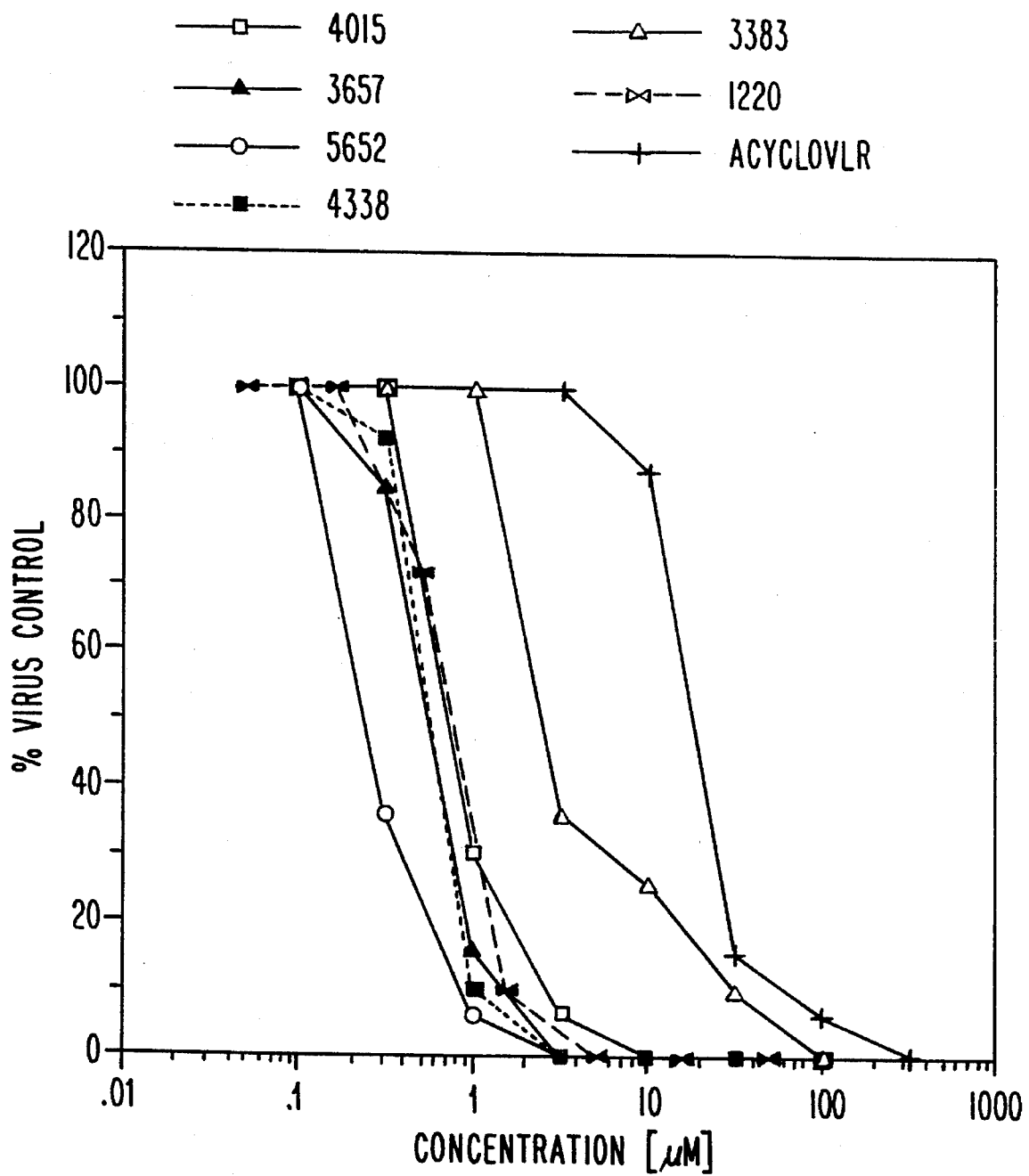
FIG. 2 is a graph showing antiviral activity of oligonucleotides ISIS 4015, 3657, 5652, 4338, 3383 and 1220 and Acyclovir against HSV-2 in MA104 cells.

Herpes simplex virus is the most studied of the human herpes viruses. The virus exists in two similar but distinct subtypes, HSV-1 and HSV-2; numerous strains of each subtype are known. Although the host range of some HSV strains is limited to certain tissues in vivo, the in vitro host range of all strains includes most human tissue types (both primary and transformed cells) as well as many non-human cells. The viral replication cycle is rapid, requiring approximately 24 hours for HSV-1 and 48 hours for HSV-2 to produce infectious progeny. The rapid replication and broad host range of HSV has resulted in an extensive molecular analysis of viral gene structure and of the control of viral gene expression during infection.

The productive infection of HSV consists of a number of differentiable stages which include: adsorption of the virus to the host cell membrane, fusion of the viral envelope with the cellular membrane, penetration of the non-enveloped virion to the nucleus of the cell, uncoating of viral nucleic acid, expression of viral genes and replication of the viral genome, nuclear packaging of the genome into newly formed viral capsids and finally, egress of the mature virion from the cell. Virally encoded proteins have been identified which control, in part, each of these stages of viral replication. The DNA sequence of the HSV-1 genome has been published and supports prior estimates that at least 71 unique viral proteins are encoded by the virus during a productive infection. McGeoch, D. J., Dolan, A., Donald, S., and Rixon, F. J. *J. Mol. Biol.* 1985, 181, 1–13; McGeoch, D. J., Dolan, A., Donald, S., and Brauer, D. H. K.; *Nucleic Acids Res.* 1986, 14, 1727–1745; McGeoch, D. J., Dalrymple, M. A., Davison, A. J., Dolan, A., Frame, M. C., McNab, D., Perry, L. J., Scott, J. E., and Taylor, P.; *J. Gen. Virol.* 1988, 69, 1531–1574; and Perry, L. J. and McGeoch, D. J., *J. Gen. Virol.* 1988, 69, 2831–2846.

The structure of HSV genes is quite simple. The transcription of each mRNA is controlled by a promoter region located immediately 5' to the mRNA cap site for that gene. Splicing of mRNAs is rare and restricted primarily to the immediate early class of transcripts. A unique mRNA species exists for each putative protein product encoded by the virus and each of the viral mRNAs is considered to act like a monocistronic species even though multiple open reading frames (ORFs) are present in many of the mRNAs. The control of viral gene expression is a finely orchestrated cascade which can be divided into three general stages: the immediate early, early and late phases. The immediate early transcripts are synthesized at the onset of viral replication, even in the presence of translational inhibitors such as cycloheximide. Thus, the synthesis of this class of transcripts is controlled by existing cellular proteins and/or proteins brought into the cell by the infecting virion. The immediate early proteins are known to influence cellular and viral gene expression in both positive and negative manners, and the expression of these proteins is important for the transcriptional activation of other HSV genes, especially the early genes. The early gene transcripts encode many of the viral products which are necessary for replication of the viral genome. Because the synthesis of late gene transcripts is controlled by both the immediate early proteins and template abundance, the late genes are transcribed maximally only after viral DNA synthesis. The proteins encoded by the late genes include the envelope glycoproteins, the capsid proteins and other proteins which are necessary to maintain viral structure or permit egress of newly formed virions from the cell.

DNA sequence analysis predicts a conservative estimate of 71 proteins encoded within the HSV-1 genome. Although a number of viral gene products have been shown to be dispensable to viral replication in vitro, only the viral thymidine kinase function has been known to be dispensable for viral growth in the human host. Logically, this leaves 70 gene targets which could be amenable to target-directed antiviral chemotherapy.

A number of structural features of HSV mRNAs are important to RNA functions such as RNA stability, maturation, transport and the efficient translation of viral proteins. The 5' caps, 5' untranslated regions, translation initiation codons and the 3' polyadenylated tails of HSV mRNAs are presumed to function in a manner analogous to similar mRNA structures which have been described for many cellular mRNAs. Splicing of HSV mRNAs is rare, but the splice sites of the immediate early transcripts represent another structural feature of the viral transcripts which could be considered as a feasible site of antisense inhibition. Additionally, unique structural features of the HSV UL48 mRNA have been reported to influence the rate of tegument protein synthesis. See Blair, E. D., Blair, C. C., and Wagner, E. K., *J. Virol.* 1987, 61, 2499–2508. The presence of similar structures in other HSV mRNAs or the ability of these structures to influence synthesis of their cognate protein species has not been examined. Thus, a large number of structural regions of an HSV mRNA are potential targets for antisense oligonucleotide inhibition of mRNA function. Indeed, the treatment of infected cells with oligonucleotides which are complementary to the splice sites of the US1 and US2 genes or the translation initiation region of the UL48 gene has resulted in the inhibition of HSV replication in vitro. See Smith, C. C., Aurelian, L., Reddy, M. P., Miller, P. S., and Ts'o, P. O. P., *Proc. Natl. Acad. Sci. USA* 1986, 83, 2787–2792; and Ceruzzi, M, and Draper, K., *Nucleosides and Nucleotides* 1989, 8, 815–818.

Viral gene products which are known to contribute a biological function to HSV replication can be categorized into three groups. These are transcriptional activator or repressor proteins, DNA replication proteins and structural proteins. The immediate early class of HSV transcripts encode proteins which function as transcriptional activators and repressors of other viral genes. Strains of virus which are deficient in the production of these proteins have been reported and with the exception of the IE175 gene product, the immediate early proteins do not appear to be essential to viral replication. The IE175 or ICP4 gene product is the major transactivator of HSV genes and therefore is believed to be an excellent target for antisense oligonucleotide inhibition of HSV. The DNA sequence of the IE175 gene is known [McGeoch et al., *Nucleic Acids Res.* 1986, 14, 1727–1745] and is available through Genbank.

The most studied group of viral proteins are those involved in genomic replication. At least seven viral open reading frames (ULS, 8, 9, 29, 30, 42 and 52) are directly involved in viral DNA replication. These seven open reading frames encode the viral DNA polymerase enzyme (UL30), a single-stranded binding protein (UL29), the $ori_s$ binding protein (UL9), a double-stranded DNA binding protein (UL42) and three proteins which comprise the helicase-primase complex (UL5, UL8 and UL52). The DNA sequence of the entire UL region containing these genes is known [McGeoch, D. J. et al., *J. Gen. Virol.* 1988, 69, 1531–1574] and these are believed to be good targets for oligonucleotide inhibition of HSV. The viral DNA polymerase, the thymidine kinase and the ribonucleotide reductase enzyme functions have been inhibited successfully with nucleoside analogs and work continues to find more potent versions of these compounds. The appearance of drug-resistant strains of HSV limits the feasibility of developing a nucleoside analog with long-term efficacy in clinical use. Because the transcription of some late viral genes depends upon gene dosage for efficient expression, antisense inhibition of viral structural protein synthesis could also be accomplished indirectly by targeting the DNA synthetic proteins.

The use of structural proteins in antiviral efforts has centered on the development of vaccines and represents an unexplored field for chemotherapeutic intervention with antisense compounds. Proteins classed into this group include those known to play roles in viral assembly and structural integrity, viral adsorption, virion fusion with the host cell membrane and virus penetration into the infected cell. One such protein, gB, is a glycoprotein which appears to be necessary for virus penetration into cells; mutant virus lacking gB are able to attach but not penetrate (Cai, W., Gu, B. and Person, S., *J. Virol.* 1988, 62, 2596–2604). The gB glycoprotein is encoded by the UL27 open reading frame. The UL20 gene is believed to encode an integral membrane protein which is necessary for viral egress from cells. The sequence of the entire UL region of the HSV-1 genome, containing these genes, is known. McGeoch, D. J. et al., *J. Gen. Virol.* 1988, 69, 1531–1574.

Accordingly, the present invention is directed to inhibition of the function of mRNAs deriving from a gene corresponding to one of the open reading frames UL5, UL8, UL9, UL20, UL27, UL29, UL30, UL42, UL52 and IE175 of HSV-1.

The DNA sequence of these genes is known only for the HSV-1 genome, but the general colinearity and gross DNA sequence homologies between the HSV-1 and HSV-2 genomes in regions encoding critical viral functions has been established such that it is likely that an oligonucleotide inhibitor for each of these HSV-1 gene functions will be found which will also inhibit functional expression of the homologous HSV-2 gene. Several HSV gene targets have been reported to be sensitive to antisense inhibitors in in vitro assays. Methylphosphonate linked and psoralen-derivatized oligonucleotides complementary to the splice junction acceptor sites of the HSV-1 US1 and US12 mRNAs have been shown to inhibit HSV-1 replication in vitro. Kulka, M., Smith. C. C., Aurelian, L., Fishelevich, R., Meade, K., Miller, P., and T'so, P. O. P., *Proc. Natl. Acad. Sci. USA* 1989, 86, 6868–6872; and Smith, C. C., Aurelian, L., Reddy, M. P., Miller, P. S., and Ts'o, P. O. P., *Proc. Nat'l Acad. Sci, USA* 1986, 83, 2787–2792. These results are intriguing because the target genes have been shown to be non-essential to HSV replication. An oligonucleotide sequence which is complementary to a gene which is essential to the replication of the virus is expected to be a better therapeutic agent than oligonucleotides targeted to non-essential gene products. Proof of this supposition was demonstrated by Ceruzzi and Draper using the HSV-1 UL48 mRNA as a target sequence. Ceruzzi, M, and Draper, K., *Nucleosides and Nucleotides* 1989, 8, 815–818. The antiviral efficacy achieved by Ceruzzi and Draper with a natural (phosphodiester) oligonucleotide was probably related to the important role of the UL48 protein in enhancing immediate early transcription of the virus.

The targeting of a number of independent viral functions offers the opportunity for broad intertypic antiviral activity by using the most highly effective antisense oligonucleotides determined by our studies in combination with each other or with an existing nucleoside therapy. Comparison of the DNA sequences of herpes simplex virus type 1 (HSV-1), varicella zoster virus (VZV) and Epstein Barr Virus (EBV) has revealed that a large number of genes are conserved among the human herpesviruses. Some examples of VZV and EBV genes which are homologous to some HSV-1 genes are set forth in FIG. 1. The predictions of ORFs are taken from GenBank annotations of published DNA sequences. Davison, A. J. & Scott, J. E., *J. Gen. Virol.* 1987, 67, 1759–1816; McGeoch, D. J., Dalrymple, M. A., Davison, A. J., Dolan, A., Frame, M. C., McNab, D., Perry, L. J., Scott, J. E., & Taylor, P., *J. Gen. Virol.* 1988, 69, 1531–1574; Baer, R., Bankier, A. T., Biggin, M. D., Deininger, P. L., Farrell, P. J., Gibson, T. J., Hatfull, G., Hudson, G. S., Satchwell, S. C., Sequin, C., Tuffnell, P. S., & Barrell, B. G., *Nature* 1984, 310, 207–211. Published sequence comparisons can be found in Davison, A. J. and McGeoch, D. J., *J. Gen Virol.* 1986, 67, 597–611 and Davison, A. J. and Wilkie, N. M. *J. Gen. Virol.* 1983, 64, 1927–1942.

A number of regions of nucleotide homology which exist within these various herpesvirus genes are now believed to be good targets for antisense oligonucleotide inhibition. It is believed that an oligonucleotide which inhibits HSV-1 and/or HSV-2 and also possesses homology to the corresponding nucleotide sequence of either VZV or EBV will be an effective inhibitor of VZV and/or EBV replication as well. Once the sequences of other human herpesviruses are known in their entirety, it is believed that the genes which have now been targeted will be retained at least in part and show significant nucleotide homology to the original HSV gene sequences.

The present invention employs oligonucleotides for inhibition of the function of messenger RNAs of herpesviruses. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar linkages. Most preferred are those with $CH_2-NH-O-CH_2$, $CH_2-N(CH_3)-O-CH_2$, $CH_2-O-N(CH_3)-CH_2$, $CH_2-N(CH_3)-N(CH_3)-CH_2$ and $O-N(CH_3)-CH_2-CH_2$ backbones (where phosphodiester is $-P-O-CH_2$). Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; a fluorescein moiety, an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

Chimeric oligonucleotides can also be employed; these molecules contain two or more chemically distinct regions, each comprising at least one nucleotide. These oligonucleotides typically contain a region of modified nucleotides that confer one or more beneficial properties (such as, for example, increased nuclease resistance, increased uptake into cells, increased binding affinity for the RNA target) and an unmodified region that retains the ability to direct RNase H cleavage.

The oligonucleotides in accordance with this invention preferably comprise from about 6 to about 50 nucleotide units. It is more preferred that such oligonucleotides comprise from about 8 to 30 nucleotide units, and still more preferred to have from about 12 to 25 nucleotide units. As will be appreciated, a nucleotide unit is a base-sugar combination suitably bound to an adjacent nucleotide unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA includes not only the information to encode a protein using the three letter genetic code, but also associated ribonucleotides which form a region known to such persons as the 5'-untranslated region, the 3'-untranslated region, the 5' cap region and intron/exon junction ribonucleotides. Thus, oligonucleotides may be formulated in accordance with this invention which are targeted wholly or in part to these associated ribonucleotides as well as to the informational ribonucleotides. In preferred embodiments, the oligonucleotide is specifically hybridizable with a translation initiation site, coding region or 5'-untranslated region. Such hybridization, when accomplished, interferes with the normal function of the messenger RNA to cause a loss of its utility to the virus. The functions of messenger RNA to be interfered with include all vital functions such as transcription of the RNA from DNA, translocation of the RNA to the site for protein translation, splicing of the RNA, translation of protein from the RNA, and possibly even independent catalytic activity which may be engaged in by the RNA. The overall effect of such interference with the RNA function is to cause the herpesvirus to lose the benefit of the RNA and to interfere with expression of the viral genome. Such interference is generally fatal to the virus.

The oligonucleotides of this invention can be used in diagnostics, therapeutics and as research reagents and kits. For therapeutic use, the oligonucleotide is administered to an animal, especially a human, suffering from a herpesvirus infection such as genital herpes, herpes simplex gingivostomatitis, herpes labialis, herpes simplex encephalitis, keratoconjunctivitis, herpetic whitlow or disseminated herpes infections of neonates and immunocompromised hosts.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms or gloves may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

The present invention is also useful in diagnostics and in research. Since the oligonucleotides of this invention hybridize to nucleic acid from herpesvirus, sandwich and other assays can easily be constructed to exploit this fact. Provision of means for detecting hybridization of oligonucleotide with herpesvirus present in a sample suspected of containing it can routinely be accomplished. Such provision may include enzyme conjugation, radiolabelling or any other suitable detection systems. Kits for detecting the presence or absence of herpesvirus may also be prepared.

The invention is further illustrated by the following examples which are meant to be illustrations only and are not intended to limit the present invention to specific embodiments.

EXAMPLES

Example 1 Oligonucleotide synthesis

Unmodified DNA oligonucleotides were synthesized on an automated DNA synthesizer (Applied Biosystems model 380B) using standard phosphoramidite chemistry with oxidation by iodine. β-Cyanoethyldiisopropyl phosphoramidites were purchased from Applied Biosystems (Foster City, Calif.). For phosphorothioate oligonucleotides, the standard oxidation bottle was replaced by a 0.2M solution of 3H-1, 2-benzodithiole-3-one 1,1-dioxide in acetonitrile for the stepwise thiation of the phosphite linkages. The thiation cycle wait step was increased to 68 seconds and was followed by the capping step.

Oligonucleotides containing inosine residues were synthesized as for unmodified DNA oligonucleotides, using inosine phosphoramidites purchased from Glen Research.

Fluorescein-conjugated oligonucleotides were synthesizes using fluorescein-labeled amidites purchased from Glen Research.

2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Trisborate buffer, pH 7.0. Oligodeoxynucleotides were judged from electrophoresis to be greater than 80% full length material.

Example 2 Cell and virus culture

HeLa (ATCC #CCL2) and Vero (ATCC #CCL81) cells used were obtained from the American Tissue Culture Collection. Cultures of HeLa cells were grown in Dulbecco's Modified Essential Medium (D-MEM) supplemented with 10% fetal bovine serum (FBS), penicillin (100 units/ml), streptomycin (100 micrograms/ml), and L-glutamine (2 mM). Cultures of Vero cells were grown in D-MEM supplemented with 5.0% FBS, penicillin, streptomycin and L-glutamine. Stock cultures of HSV-1 (strain KOS) and HSV-2 (strain HG52) were grown in Veto cells using low multiplicity infections (multiplicity of infection [MOI]=0.02 plaque forming units[pfu]/cell).

Example 3 Testing of oligonucleotides for activity against HSV-1

Phosphorothioate oligonucleotides were designed to be specifically hybridizable with regions of the HSV-1RNA. These oligonucleotides are shown in Table 1:

TABLE 1

| Phosphorothioate oligonucleotides targeted to HSV-1 (sequences written 5' TO 3') | | | | |
|---|---|---|---|---|
| Oligo # | Sequence | Target | Target Function | SEQ ID NO: |
| 1220 | CAC GAA AGG CAT GAC CGG GGC | UL9, AUG | Ori binding protein | 1 |
| 4274 | CAT GGC GGG ACT ACG GGG GCC | UL27, AUG | virion gB | 2 |
| 4338 | ACC GCC AGG GGA ATC CGT CAT | UL42, AUG | DNA binding protein | 3 |
| 4346 | GAG GTG GGC TTC GGT GGT GA | UL42, 5'UTR | DNA binding protein | 4 |
| 3657 | CAT CGC CGA TGC GGG GCG ATC | IE175, AUG | Transc. transactivator | 5 |
| 4015 | GTT GGA GAC CGG GGT TGG GG | UL29, 5'UTR | ssDNA binding protein | 6 |
| 4398 | CAC GGG GTC GCC GAT GAA CC | UL29, 5'UTR | ssDNA binding protein | 7 |
| 4393 | GGG GTT GGG GAA TGA ATC CC | UL29, 5'UTR | ssDNA binding protein | 8 |
| 4348 | GGG TTG GAG ACC GGG GTT GG | UL29, 5'UTR | ssDNA binding protein | 9 |

TABLE 1-continued

Phosphorothioate oligonucleotides targeted to HSV-1 (sequences written 5' TO 3')

| Oligo # | Sequence | Target | Target Function | SEQ ID NO: |
|---|---|---|---|---|
| 4349 | GGT TGG AGA CCG GGG TTG GG | UL29, 5'UTR | ssDNA binding protein | 10 |
| 4341 | TGG AGA CCG GGG TTG GGG AA | UL29, 5'UTR | ssDNA binding protein | 11 |
| 4342 | TTG GAG ACC GGG GTT GGG GA | UL29, 5'UTR | ssDNA binding protein | 12 |
| 4350 | GAC GGT CAA GGG GAG GGT TGG | UL29, 5'UTR | ssDNA binding protein | 13 |
| 4435 | GGG GAG ACC GAA ACC GCA AA | UL20, 5'UTR | Viral egress | 14 |
| 4111 | CCT GGA TGA TGC TGG GGT AC | UL30, coding | DNA polymerase | 15 |
| 4112 | GAC TGG GGC GAG GTA GGG GT | UL30, coding | DNA polymerase | 16 |
| 4399 | GTC CCG ACT GGG GCG AGG AT | UL30, coding | DNA polymerase | 17 |
| 1082 | GCC GAG GTC CAT GTC GTA CGC | UL13, AUG | Protein kinase | 43 |

The oligonucleotides shown in Table 1 were tested for activity against HSV-1 (KOS strain) using an ELISA assay. Confluent monolayers of human dermal fibroblasts (NHDF) were infected with HSV-1 (KOS) at a multiplicity of infection of 0.05 pfu/cell. After a 90-minute adsorption at 37° C., virus was removed and culture medium containing oligonucleotide at the indicated concentrations was added. Two days after infection, medium was removed and cells were fixed by addition of 95% ethanol. HSV antigen expression was quantitated using an enzyme-linked immunoassay. Primary reactive antibody in the assay was a monoclonal antibody specific for HSV-1 glycoprotein B. Detection was achieved using biotinylated goat anti-mouse IgG as secondary antibody followed by reaction with streptavidin-conjugated β-galactosidase. Color was developed by addition of chlorophenol red-β-D-galactopyranoside and absorbance at 570 nm was measured. Results are expressed as percent of untreated control. From these results, an EC50 (effective oligonucleotide concentration giving 50% inhibition) is calculated for each oligonucleotide. These values, expressed in µM, are given in Table 2. Oligonucleotides having EC50s of 1 µM or less in this ELISA assay were judged to have particularly good activity and are preferred.

TABLE 2

Oligonucleotide inhibition of HSV-1
All oligonucleotides are phosphorothioates

| Oligo # | Target | SEQ ID NO: | EC50 (µM)* |
|---|---|---|---|
| 1220 | UL9, AUG | 1 | 0.24, 0.16 |
| 4274 | UL27, AUG | 2 | 0.15, 0.15 |
| 4338 | UL42, AUG | 3 | 0.20, 0.20 |
| 4346 | UL42, 5'UTR | 4 | 0.50 |
| 3657 | IE175, AUG | 5 | 0.20 |
| 4015 | UL29, 5'UTR | 6 | 0.22, 0.22 |
| 4398 | UL29, 5'UTR | 7 | 0.10 |
| 4393 | UL29, 5'UTR | 8 | 0.20 |
| 4348 | UL29, 5'UTR | 9 | 0.40 |
| 4349 | UL29, 5'UTR | 10 | 0.25 |
| 4341 | UL29, 5'UTR | 11 | 0.20 |
| 4342 | UL29, 5'UTR | 12 | 0.20 |
| 4350 | UL29, 5'UTR | 13 | 0.25 |
| 4435 | UL20, 5'UTR | 14 | 0.22 |
| 4111 | UL30, coding | 15 | 0.60 |
| 4112 | UL30, coding | 16 | 0.30 |
| 4399 | UL30, coding | 17 | 0.25 |

TABLE 2-continued

Oligonucleotide inhibition of HSV-1
All oligonucleotides are phosphorothioates

| Oligo # | Target | SEQ ID NO: | EC50 (µM)* |
|---|---|---|---|
| 1082 | UL13, AUG | 43 | 2.50, 1.80 |

*Some experiments were done in duplicate

Example 4 Inhibition of HSV by shortened oligonucleotides

A series of shortened oligonucleotides were synthesized based on the sequences shown to have good activity in the ELISA assay. These oligonucleotides and their activities against HSV-1 (assayed by ELISA) are shown in Table 3, compared to their respective parent oligonucleotides. Oligonucleotides having an EC50 of 1 µM or less in this ELISA assay were judged to have particularly good activity and are preferred.

TABLE 3

Activity of shortened oligonucleotides against HSV
EC50 values expressed in μM

| Oligo # | Sequence | Length | EC50 (μm)* | SEQ ID NO: |
|---|---|---|---|---|
| 1220 | CAC GAA AGG CAT GAC CGG GGC | 21 | 0.24, 0.16 | 1 |
| 4881 | GAA AGG CAT GAC CGG GGC | 18 | 0.70, 0.65 | 18 |
| 4874 | AGG CAT GAC CGG GGC | 15 | 1.10. 0.83 | 19 |
| 4873 | CAT GAC CGG GGC | 12 | 1.40, 1.00 | 20 |
| 5305 | CAC GAA AGG CAT GAC CGG G | 19 | >3.0 | 21 |
| 5301 | CAC GAA AGG CAT GAC CGG | 18 | >3.0 | 22 |
| 5302 | CAC GAA AGG CAT GAC | 15 | >3.0 | 23 |
| 4274 | CAT GGC GGG ACT ACG GGG GCC | 21 | 0.15, 0.15 | 2 |
| 4851 | T GGC GGG ACT ACG GGG GC | 18 | 0.55, 0.50 | 24 |
| 4882 | CAT GGC GGG. ACT ACG | 15 | 1.70, 1.40 | 25 |
| 4872 | GGC GGG ACT ACG GGG | 15 | 1.90, 1.70 | 26 |
| 4338 | ACC GCC AGG GGA ATC CGT CAT | 21 | 0.20, 0.20 | 3 |
| 4883 | GCC AGG GGA ATC CGT CAT | 18 | 1.80, 1.80 | 27 |
| 4889 | AGG GGA ATC CGT CAT | 15 | 2.00, 2.00 | 28 |
| 4890 | GCC AGG GGA ATC CGT | 15 | 0.75, 0.70 | 29 |
| 3657 | CAT CGC CGA TGC GGG GCG ATC | 21 | 0.20 | 5 |
| 4891 | CAT CGC CGA TGC GGG GCG | 18 | 0.30 | 30 |
| 4894 | CAT CGC CGA TGC GGG | 15 | >3.0 | 31 |
| 4895 | CGC CGA TGC GGG GCG | 15 | 0.55 | 32 |
| 4896 | GC CGA TGC GGG G | 12 | 1.20 | 33 |
| 4015 | GTT GGA GAC CGG GGT TGG GG | 21 | 0.22, 0.22 | 6 |
| 4549 | GGA GAC CGG GGT TGG GG | 17 | 0,22, 0.27 | 34 |
| 4771 | GTT GGA GAC CGG GGT TG | 17 | 0.70 | 35 |
| 4885 | A GAC CGG GGT TGG GG | 15 | 0.42, 0.52 | 36 |
| 4717 | GG GGT TGG GG | 10 | 0.60 | 37 |
| 5365 | GA GAC CGG GGT TGG GG | 16 | 0.47 | 38 |
| 4398 | CAC GGG GTC GCC GAT GAA CC | 20 | 0.10 | 7 |
| 4772 | GGG GTC GCC GAT GAA CC | 17 | 0.40 | 39 |
| 4897 | CAC GGG GTC GCC GAT | 15 | 0.13 | 40 |
| 4773 | CAC GGG GTC GCC GAT GA | 17 | 0.20 | 41 |
| 4721 | CAC GGG GTC G | 10 | 0.40 | 42 |
| 1082 | GCC GAG GTC CAT GTC GTA CGC | 43 | 2.50, 1.80 | 43 |
| 3383 | TGG GCA CGT GCC TGA CAC GGC (scrambled 1082 sequence) | 21 | 3.00 | 44 |

*Some experiments done in duplicate

A number of shortened oligonucleotides had EC50s of 1 μM or less; it was surprisingly found that some oligonucleotides as short as 10 nucleotides in length showed good activity.

Example 5 Activity of inosine-substituted oligonucleotides

A series of oligonucleotides were prepared in which one or more guanosines were replaced with an inosine residue. These sequences were assayed for activity in ELISA assays as described in Example 3. These oligonucleotides, their parent sequences and EC50 values are shown in Table 4.

Example 6 Fluorescein-conjugated oligonucleotides

Several oligonucleotides were synthesized with a fluorescein moiety conjugated to the oligonucleotide. These sequences were assayed for activity in ELISA assays as described in Example 3. These oligonucleotides, their parent sequences and EC50 values are shown in Table 5. In this assay, oligonucleotides with EC50s of 1 μM or less were judged to be particularly active and are preferred.

TABLE 4

Activity of inosine-substituted oligonucleotides against HSV

| Oligo # | Sequence | Target | Type | EC50 (μM) | SEQ ID NO: |
|---|---|---|---|---|---|
| 1220 | CAC GAA AGG CAT GAC CGG GGC | UL9, AUG | Parent | 0.24, 0.16 | 1 |
| 5297 | CAC GAA AGG CAT GAC CGI GGC | UL9, AUG | Inosine #18 | >3.0 | 45 |
| 5308 | CAC GAA AGG CAT GAC CGG GIC | UL9, AUG | Inosine #20 | >3.0 | 46 |
| 4015 | GTT GGA GAC CGG GGT TGG GG | UL29, 5'UTR | Parent | 0.22, 0.22 | 6 |
| 4925 | GTT GGA GAC CGG IGT TGG IG | UL29, 5'UTR | Inosine #13, 19 | 1.60 | 47 |
| 5295 | GTT GGA GAC CGG GIT TGG GG | UL29, 5'UTR | Inosine #14 | >3.0 | 48 |
| 5296 | GTT GGA GAC CGG GGT TGG IG | UL29, 5'UTR | Inosine #19 | 0.80 | 49 |
| 5309 | GTT GGA GAC CGI GGT TGG GG | UL29, 5'UTR | Inosine #12 | >3.0 | 50 |
| 5310 | GTT GGA GAC CGG GGT TGG GI | UL29, 5'UTR | Inosine #20 | 0.40 | 51 |

In this assay, oligonucleotides with EC50s of 1 μM or less were judged to be particularly active and are preferred.

TABLE 5

Activity of fluorescein-conjugated oligonucleotides against HSV

| Oligo # | Sequence | Target | Type | EC50 (µM) | SEQ ID NO: |
|---|---|---|---|---|---|
| 1220 | CAC GAA AGG CAT GAC CGG GGC | UL9, AUG | Parent | 0.24, 0.16 | 1 |
| 5338 | CAC GAA AGG CAT GAC CGG GGC | UL9, AUG | Fluorescein | 0.16 | 1 |
| 3657 | CAT CGC CGA TGC GGG GCG ATC | IE175, AUG | Parent | 0.20 | 5 |
| 5340 | CAT CGC CGA TGC GGG GCG ATC | IE175, AUG | Fluorescein | 0.18 | 5 |
| 4398 | CAC GGG GTC GCC GAT GAA CC | UL29, 5'UTR | Parent | 0.10 | 7 |
| 5324 | CAC GGG GTC GCC GAT GAA CC | UL29, 5'UTR | Fluorescein | 0.16 | 7 |
| 1082 | GCC GAG GTC CAT GTC GTA CGC | UL13, AUG | Parent | 2.50, 1.80 | 43 |
| 5339 | GCC GAG GTC CAT GTC GTA CGC | UL13, AUG | Fluorescein | 0.65 | 43 |

Example 7 Chimeric 2'-O-methyl oligonucleotides with deoxy gaps

A series of phosphorothioate oligonucleotides were synthesized having a 2'-O-methyl substitution on the sugar of each nucleotide in the flanking regions, and 2'-deoxynucleotides in the center portion of the oligonucleotide (referred to as the "deoxy gap"). Deoxy gaps varied from zero to seven nucleotides in length. These chimeric oligonucleotides were assayed by ELISA as described in Example 3 and results are shown in Table 6. In this assay, oligonucleotides with EC50s of 1 µM or less were judged to be particularly active and are preferred.

TABLE 6

Activity of 2'-O-me oligonucleotides against HSV
(2'-O-me nucleotides shown in bold)

| Oligo # | Sequence | Target | Type | EC50 (µM) | SEQ ID NO: |
|---|---|---|---|---|---|
| 1220 | CAC GAA AGG CAT GAC CGG GGC | UL9, AUG | Parent(deoxy) | 0.24, 0.16 | 1 |
| 4240 | CAC GAA AGG CAT GAC CGG GGC | UL9, AUG | Deoxy gap | | 1 |
| 3657 | CAT CGC CGA TGC GGG GCG ATC | IE175, AUG | Parent(deoxy) | 0.20 | 5 |
| 5377 | CAT CGC CGA TGC GGG GCG ATC | IE175, AUG | 2'-O-me | 1.20 | 5 |
| 4237 | CAT CGC CGA TGC GGG GCG ATC | IE175, AUG | Deoxy gap | | 5 |
| 4015 | GTT GGA GAC CGG GGT TGG GG | UL29, 5'UTR | Parent(deoxy) | 0.22, 0.22 | 6 |
| 4538 | GTT GGA GAC CGG GGT TGG GG | UL29, 5'UTR | Deoxy gap | 0.16 | 6 |
| 5378 | GTT GGA GAC CGG GGT TGG GG | UL29, 5'UTR | 2'-O-me | 0.40 | 6 |
| 4398 | CAC GGG GTC GCC GAT GAA CC | UL29, 5'UTR | Parent(deoxy) | 0.10 | 7 |
| 5039 | CAC GGG GTC GCC GAT GAA CC | UL29, 5'UTR | 2'-O-me | 2.70 | 7 |
| 5189 | CAC GGG GTC GCC GAT GAA CC | UL29, 5'UTR | Deoxy gap | 0.16 | 7 |

Additional chimeric oligonucleotides were synthesized having SEQ ID NO: 6 and SEQ ID NO:7. These oligonucleotides were 2'-O-methyl oligonucleotides with deoxy gaps as described above, but instead of a uniform phosphorothioate backbone, these compounds had phosphorothioate internucleotide linkages in the deoxy gap region and phosphodiester linkages in the flanking region. These oligonucleotides were not active against HSV in this ELISA assay.

Example 8 Activity of oligonucleotides against various strains of HSV

Oligonucleotides were tested against HSV-1 and five strains of HSV-1, of which two (HSV1-DM2.1 and HSV1-PAAr) are resistant to acyclovir (ACV). Oligonucleotides were assayed by ELISA as described in Example 3 and results are shown in Table 7. In this assay, oligonucleotides with EC50s of 1 µM or less were judged to be particularly active and are preferred.

TABLE 7

Oligonucleotide activity against various HSV strains
Results are given as EC50, expressed in µM

| | Compound: | | | | | | |
|---|---|---|---|---|---|---|---|
| | 4015 | 1220 | 3657 | 4338 | 4274 | 1082 | ACV |
| | | | SEQ ID NO: | | | | |
| | 6 | 1 | 5 | 3 | 2 | 43 | |
| HSV strain | | | | | | | |
| HSV-1 (KOS) | 0.25 | 0.34 | 0.38 | 0.24 | 0.21 | 2.1 | 2.5 |
| HSV-2 | 0.2 | 0.1 | 0.2 | 0.2 | 0.2 | 2.0 | 2.0 |
| HSV1-F | 0.22 | 0.22 | 0.22 | 0.25 | 0.25 | >3.0 | 0.7 |
| HSV1-McKrae | 0.45 | 0.30 | 0.40 | 0.60 | | >3.0 | 1.8 |
| HSV1-DM2.1 | 0.10 | 0.10 | 0.10 | 0.70 | 0.40 | >3.0 | >3.0 |
| HSV1-PAAr | 0.35 | 0.12 | 0.10 | 0.30 | 0.25 | >3.0 | >3.0 |

Example 9 Infectious yield assay

The compounds from Table 7 were tested for ability to inhibit HSV replication (virus yield). Confluent monolayers of human dermal fibroblasts were infected with HSV-1 (KOS) at a multiplicity of infection of 0.5 pfu/cell. After a 90-minute adsorption at 37° C., virus was removed and 1 ml of culture medium containing compound (oligonucleotide or ACV) at the desired concentration was added. Control wells received 1 ml of medium without compound. Two days after infection, medium and cells were harvested and duplicate wells of each experimental point were combined. The suspension was frozen and thawed three times, then drawn through a 22-gauge needle five times. Virus titer was determined by plaque assay on Vero cell monolayers. Dilutions of each virus preparation were prepared and duplicates were adsorbed onto confluent Vero cell monolayers for 90 minutes. After adsorption, virus was removed, cells were rinsed once with PBS, and overlaid with 2 ml of medium containing 5.0% FBS and methylcellulose. Cells were incubated at 37° C. for 72 hours before plaques were fixed with formaldehyde and stained with crystal violet. The number of plaques from treated wells was compared to the number of plaques from control wells. Results are calculated as percent of virus titer from untreated control cells. From these results, an EC70 (effective oligonucleotide concentration giving 70% inhibition) is calculated for each oligonucleotide. These values, expressed in μM, are given in Table 8.

TABLE 9

Effect of oligonucleotide (10 μM) on Virus Yield Expressed as percent of infected control

| Compound | NHDF (-serum)* | NHDF** | HeLa** | Vero* | SEQ ID NO: |
|---|---|---|---|---|---|
| ACV | 0.05% | 0.3% | 8.0% | 0.28% | |
| 4015 | 0.07 | 6.5 | 0.2 | 1.25 | 6 |
| 4338 | 1.85 | 1.75 | 0.4 | 0.75 | 3 |
| 4274 | 3.0 | | 21.0 | 6.0 | 2 |
| 1220 | 5.0 | 25.0 | 8.5 | 11.0 | 1 |
| 3657 | 5.5 | 50.0 | 4.5 | 4.0 | 5 |
| 1082 | >100 | | >100 | >100 | 43 |
| 3383 | >100 | >100 | >100 | >100 | 44 |

*MOI = 0.5
**MOI = 1.0

Example 12 Anti-HSV activity of G4 oligonucleotides

A series of oligonucleotides with G4 sequence motifs were synthesized and tested against HSV-1. Infectious virus yield assays were conducted as described in Example 9,

TABLE 8

Effect of oligonucleotides on HSV-1 (KOS) infectious yield

| Oligo # | Sequence | Target | EC70 | SEQ ID NO: |
|---|---|---|---|---|
| 1220 | CAC GAA AGG CAT GAC CGG GGC | UL9, AUG | 1.9 μM | 1 |
| 4274 | CAT GGC GGG ACT ACG GGG GCC | UL27, AUG | 1.5 | 2 |
| 3657 | CAT CGC CGA TGC GGG GCG ATC | IE175, AUG | 1.8 | 5 |
| 4015 | GTT GGA GAC CGG GGT TGG GG | UL29, 5'UTR | 1.7 | 6 |
| 1082 | GCC GAG GTC CAT GTC GTA CGC | UL13, AUG | >3.0 | 43 |
| ACV | | | 0.4 | |

Example 10 Cytotoxicity

The compounds shown in Table 8 were tested for cytotoxicity using the MTT assay. This method measures cell viability and is based on the reduction of the tetrazolium salt, 3-(4,5-dimethyl-thiazol-2-yl)-2,5-diphenyl tetrazolium bromide (MTT) to MTT formazan by mitochondrial enzymes of viable host cells (Mossmann, T., *J. Immunol. Methods*. 1983, 65, 55). Cells were treated with MTT followed by SDS to dissolve the crystals of MTT formazan. The blue color of the MTT formazan was measured spectrophotometrically at 570 nm on an automated plate reader. Viability was determined by comparing the absorbance (optical density, O.D.) of each drug cytotoxicity control with the mean O.D. of the cell control cultures and expressed as percent of control. All of the compounds had IC50 (concentration of compound which killed 50% of cells) of 100 μM or above.

Example 11 Effect of oligonucleotides on virus yield in different cell types

Infectious virus yield assays were conducted as described in Example 9 using HSV-1 (KOS), at an oligonucleotide or ACV concentration of 10 μM. Three cell types were tested: NHDF, HeLa and Vero. NHDF cells were tested with and without serum in the medium. Results are shown in Table 9.

using an oligonucleotide concentration of 3 μM. Results are shown in Table 10, expressed as percent of virus-infected control.

TABLE 10

| G4 oligonucleotides: Virus yield assay | | | |
|---|---|---|---|
| Oligo # | Sequence | % Control | SEQ ID NO: |
| 5651 | TT GGGG TT GGGG TT GGGG TT GGGG | 0.12 | 52 |
| 5674 | TT GGGG TT GGGG | 104.5 | 53 |
| 4717 | GGGG TT GGGG | 10.0 | 37 |
| 5320 | TT GGGG TT | 113.0 | 54 |
| 4803 | GGGG | 104.0 | |
| 4015 | GTT GGA GAC C GGGG TT GGGG | 7.3 | 6 |
| 4274 | CAT GGC GGG ACT AC GGGGG CC | 8.2 | 2 |

Additional G4 oligonucleotides were tested against HSV-1 in the infectious virus yield assay, and from these results EC70, EC90 and EC99 values were calculated. These are shown in Table 11.

TABLE 11

| G4 Oligonucleotides: virus yield assay | | | | | |
|---|---|---|---|---|---|
| Oligo # | Sequence | EC70 | EC90 | ED99 | SEQ ID NO: |
| 5651 | TT GGGG TT GGGG TT GGGG TT GGGG | 1.0µM | 1.2µM | 1.8µM | 52 |
| 5652 | TT GGGG TT GGGG TT GGGG TT | 1.0 | 1.2 | 1.8 | 55 |
| 5676 | GGGG TT GGGG TT GGGG | 0.6 | 1.2 | 2.5 | 56 |
| 5653 | TT GGGG TT GGGG TT GGGG | 0.7 | 1.6 | 3.2 | 57 |
| 4015 | GTT GGA GAC C GGGG TT GGGG | 2.5 | 4.2 | 10.0 | 6 |
| 3383 | TGG GCA CGT GCC TGA CAC GGC | >10.0 | >10.0 | >10.0 | 44 |
| ACV | | 0.4 | 1.2 | 4.2 | |

Example 13 Antiviral activity of oligonucleotides against HSV-2

ISIS 5652 was tested along with other compounds for activity against HSV-2 in cells using a cytopathic effect (CPE) inhibition assay. MA-104 cells were seeded in 96-well plates and infected with the E194 strain of HSV-2. Compound dilutions (4 wells/dilution) were added to cells and virus was added to all compound test wells and to virus control wells. Plates were incubated at 37° C. until virus control wells showed adequate cytopathic effects (CPE). Virus CPE was graded on a scale of 0–4, with 0 being no CPE and 4 being 100% CPE. The results are presented as dose-response curves in FIG. 2. Oligonucleotide 5652 showed the greatest activity with an ED50 (effective dose to reduce the average viral CPE to 50% of that seen in virus controls) of 0.3 µM. All compounds showed antiviral activity greater than that of ACV (ED50=97.7 µM).

Example 14 Time of oligonucleotide addition study

Figure 3:
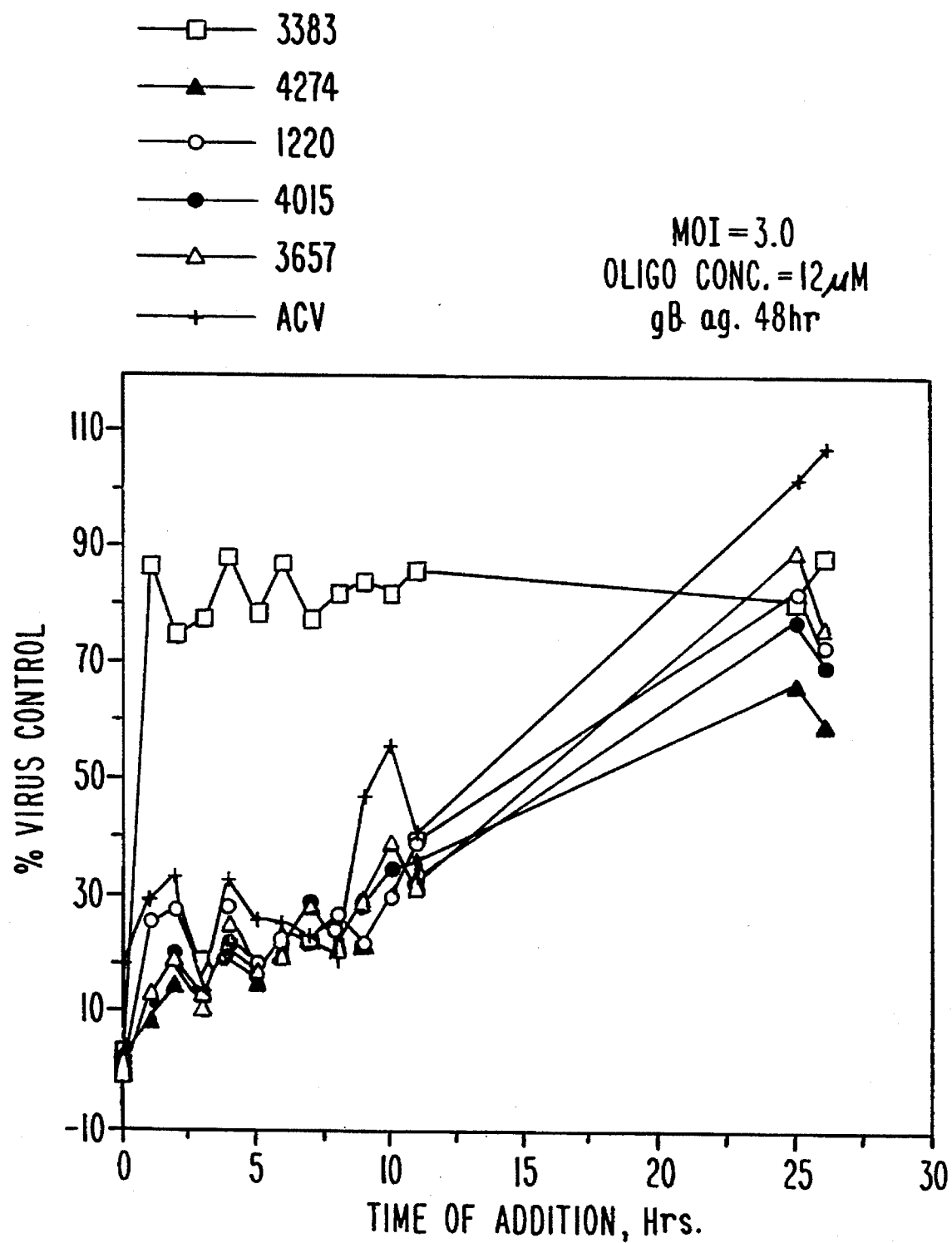
FIG. 3 is a graph showing the effects of time of addition of oligonucleotides ISIS 3383, 4274, 1220, 4015 and 3657 and Acyclovir on HSV-1 in NHDF cells.

NHDF cells were infected with HSV-1 (KOS) at a MOI of 3.0 pfu/cell. Oligonucleotides or ACV were added at a concentration of 12 mM at different times after infection. HSV was detected by ELISA 48 hours after infection. It was found that all oligonucleotides, including scrambled control oligonucleotide 3383, inhibited HSV replication when added to cells at the time of virus infection (t=0), but only oligonucleotides complementary to HSV genes (ISIS 4274, 1220, 4015 and 3657) inhibited HSV replication when added after virus infection. Oligonucleotides showed good antiviral activity when added 8 to 11 hours after infection. This pattern is similar to that observed with ACV, as shown in FIG. 3.

Example 15 Activity of oligonucleotides against other viruses

Antiviral activity of oligonucleotides was determined by CPE inhibition assay for influenza virus, adenovirus, respiratory syncytial virus, human rhinovirus, vaccinia virus, HSV-2 and varicella zoster virus. The MTT cell viability assay was used to assay effects on HIV. HSV-2, adenovirus, vaccinia virus and rhinovirus were assayed in MA104 cells. Respiratory syncytial virus was assayed in HEp-2 cells and influenza virus was assayed in MDCK cells. CEM cells were used in MYY assays of HIV inhibition. Oligonucleotide was added at time of virus infection.

MDCK (normal canine kidney) cells and HEp-2, a continuous human epidermoid carcinoma cell line, were obtained from the American Type Culture Collection, Rockville, Md. MA-104, a continuous line of African green monkey kidney cells, was obtained from Whittaker M. A. Bioproducts, Walkersville, Md.

HSV-2 strain E194 and influenza strain A/NWS/33 (H1N1) were used. Adenovirus, Type 5 (A-5), strain Adenoid 75; respiratory syncytial virus (RSV) strain Long; rhinovirus 2 (R-2), strain HGP; and vaccinia virus, strain Lederiechorioallantoic were obtained from the American Type Culture Collection, Rockville Md.

Cells were grown in Eagle's minimum essential medium with non-essential amino acids (MEM, GIBCO-BRL, Grand Island N.Y.) with 9% fetal bovine serum (FBS, Hyclone Laboratories, Logan Utah), 0.1% NaHCO₃ for MA104 cells; MEM 5% FBS, 0.1% NaHCO₃ for MDCK cells, and MEM, 10% FBS, 0.2% NaHCO₃ for HEp-2 cells. Test medium for HSV-2, A-5, R-2 and vaccinia virus dilution was MEM, 2% FBS, 0.18% NaHCO₃, 50 µg gentamicin/ml. RSV was diluted in MEM, 5% FBS, 0.18% NaHCO₃, 50 µg gentamicin/ml. Test medium for dilution of influenza virus was MEM without serum, with 0.18% NaHCO₃, 20 µg trypsin/ml, 2.0 µg EDTA/ml, 50 µg gentamicin/ml.

Ribavirin was obtained from ICN Pharmaceuticals, Costa Mesa, Calif. Acyclovir and 9β-D-arabinofuranosyladenine (ara-A) were purchased from Sigma Chemical Co., St. Louis, Mo. Ribavirin, acyclovir and ara-A were prepared and diluted in MEM without serum, plus 0.18% $NaHCO_3$, 50 μg gentamicin/ml. Oligonucleotides were diluted in the same solution.

Cells were seeded in 96-well flat bottom tissue culture plates, 0.2 ml/well, and incubated overnight in order to establish monolayers of cells. Growth medium was decanted from the plates. Compound dilutions were added to wells of the plate (4 wells/dilution, 0.1 ml/well for each compound) as stocks having twice the desired final concentration. Compound diluent medium was added to cell and virus control wells (0.1 ml/well). Virus, diluted in the specified test medium, was added to all compound test wells 3 wells/dilution) and to virus control wells at 0.1 ml/well. Test medium without virus was added to all toxicity control wells (1 well/dilution for each compound test) and to cell control wells at 0.1 ml/well. The plates were incubated at 37° C. in a humidified incubator with 5% $CO_2$, 95% air atmosphere until virus control wells had adequate CPE readings. Cells in test and virus control wells were then examined microscopically and graded for morphological changes due to cytotoxicity. Effective dose, 50% endpoint (ED50) and cytotoxic dose, 50% endpoint (CD50) were calculated by regression analysis of the viral CPE data and the toxicity control data, respectively. The ED50 is that concentration of compound which is calculated to produce a CPE grade halfway between that of the cell controls (0) and that of the virus controls. CD50 is that concentration of compound calculated to be halfway between the concentration which produces no visible effect on the cells and the concentration which produces complete cytotoxicity. The therapeutic index (TI) for each substance was calculated by the formula: TI=CD50/ED50.

The results are shown in Table 12. Oligonucleotides with ED50 values of less than 50 μM were judged to be active in this assay and are preferred. All six oligonucleotides tested had activity against HSV-2. None of the oligonucleotides tested were active against rhinovirus 2 or adenovirus. The three oligonucleotides (3657, 4015 and 5652) tested against influenza virus and RSV were active. The five oligonucleotides (4015, 3657, 4338, 1220) tested against vaccinia virus were active.

TABLE 12

Oligonucleotide activity against RNA, and DNA viruses

| Compound: | DNA Viruses: | | | | RNA Viruses: | | | |
|---|---|---|---|---|---|---|---|---|
| | HSV-2 | VZV | A-5 | Vacc. | RSV | Rhino | HIV | Influenza |
| 3383 | | | | | | | | |
| ED50 | 2.8μM | — | >100 | >100 | 0.7 | >100 | — | 19 |
| TI | >36 | — | — | — | 60 | — | >5 | |
| 4015 | | | | | | | | |
| ED50 | 0.8 | 29 | >100 | 15 | 0.6 | >100 | 0.16 | 0.6 |
| TI | >125 | 1.0 | <1.0 | >6.7 | 93 | — | 100 | 93 |
| 3657 | | | | | | | | |
| ED50 | 0.6 | >100 | >100 | 18 | 0.8 | >100 | — | 1.0 |
| TI | >167 | 1.0 | <1.0 | >5.6 | >125 | — | — | 56 |
| 4338 | | | | | | | | |
| ED50 | 0.6 | — | 68 | 19 | 1.0 | >100 | — | 0.5 |
| TI | >53 | — | >1.5 | >5.3 | 13 | — | — | >200 |
| 1220 | | | | | | | | |
| ED50 | 0.7 | — | >50 | 46 | — | >50 | — | — |
| TI | >71 | — | — | >1.1 | — | — | — | — |
| 5652 | | | | | | | | |
| ED50 | 0.3 | 18 | >100 | — | 1.9 | >100 | 0.18 | 0.6 |
| TI | >333 | — | <1.0 | — | >53 | — | 227 | 93 |
| ACV | | | | | | | | |
| ED50 | 97.7 | — | — | — | — | — | — | — |
| TI | >45 | — | — | — | — | — | — | — |
| Ribavirin | | | | | | | | |
| ED50 | — | — | 82 | — | 49 | 229 | — | 7.78 |
| TI | — | — | 28 | — | 20 | 10 | — | 202 |
| Ara-A | | | | | | | | |
| ED50 | — | — | — | 15.8 | — | — | — | — |
| TI | — | — | — | 125 | — | — | — | — |

What is claimed is:

1. An oligonucleotide wherein the nucleotide sequence is SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 47, SEQ ID NO: 49, SEQ ID NO: 51, SEQ ID NO: 52, SEQ ID NO: 55, SEQ ID NO: 56 or SEQ ID NO: 57.

2. A method of inhibiting replication of a herpesvirus in vitro comprising contacting a cell infected with a herpesvirus with an oligonucleotide wherein the nucleotide sequence is SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 47, SEQ ID NO: 49, SEQ ID NO: 51, SEQ ID NO: 52, SEQ ID NO: 55, SEQ ID NO: 56 or SEQ ID NO: 57 so that replication of herpesvirus in inhibited.

* * * * *

UNITED STATES PATENT AND TRADEMARK OFFICE
CERTIFICATE OF CORRECTION

PATENT NO. : 5,514,577
DATED : May 7, 1996
INVENTOR(S) : Draper et al.

It is certified that error appears in the above-indentified patent and that said Letters Patent is hereby corrected as shown below:

Column 7, line 46, after "where phosphodiester is", delete "-P-O-CH$_2$" and insert therefor --O-P-O-CH$_2$--.

Signed and Sealed this

Twenty-fourth Day of September, 1996

Attest:

BRUCE LEHMAN

Attesting Officer     Commissioner of Patents and Trademarks